US00PP24074P2

(12) United States Plant Patent
Lannes

(10) Patent No.: US PP24,074 P2
(45) Date of Patent: Dec. 10, 2013

(54) ***MANDEVILLA* PLANT NAMED 'LANCALIFORNIA'**

(50) Latin Name: *Mandevilla Sanderi*
Varietal Denomination: Lancalifornia

(75) Inventor: Robert Lannes, Malause (FR)

(73) Assignee: D.H.M. Innovation S.A.S., Malause (FR)

( * ) Notice: Subject to any disclaimer, the term of this patent is extended or adjusted under 35 U.S.C. 154(b) by 84 days.

(21) Appl. No.: 13/374,919

(22) Filed: Jan. 23, 2012

(51) Int. Cl.
*A01H 5/00* (2006.01)

(52) U.S. Cl.
USPC ..... Plt./232

(58) Field of Classification Search
USPC ..... Plt./232
See application file for complete search history.

*Primary Examiner* — Susan McCormick Ewoldt
(74) *Attorney, Agent, or Firm* — C. A. Whealy

(57) ABSTRACT

A new and distinct cultivar of *Mandevilla* plant named 'Lancalifornia', characterized by its compact plant habit; moderately vigorous to vigorous growth habit; glossy dark green-colored leaves; early and freely flowering habit; and large yellow-colored flowers.

2 Drawing Sheets

Botanical designation: *Mandevilla Sanderi.*
Cultivar denomination: 'LANCALIFORNIA'.

BACKGROUND OF THE INVENTION

The present invention relates to a new and distinct cultivar of *Mandevilla* plant, botanically known as *Mandevilla Sanderi* and hereinafter referred to by the name 'Lancalifornia'.

The new *Mandevilla* plant is a product of a planned breeding program conducted by the Inventor in Malause, France. The objective of the breeding program is to create new *Mandevilla* plants with numerous yellow-colored flowers.

The new *Mandevilla* plant originated from a cross-pollination conducted by the Inventor in Malause, France on Oct. 21, 2008 of *Mandevilla Sanderi* 'Rosea Foncé', not patented, as the female, or seed parent with an unnamed selection of *Mandevilla Sanderi*, not patented, as the male, or pollen, parent. The new *Mandevilla* plant was discovered and selected by the Inventor as a single flowering plant from within the progeny of the stated cross-pollination in a controlled greenhouse environment in Malause, France in May, 2010.

Asexual reproduction of the new *Mandevilla* plant by cuttings in a controlled greenhouse environment in Malause, France, since July, 2010 has shown that the unique features of this new *Mandevilla* plant are stable and reproduced true to type in successive generations.

SUMMARY OF THE INVENTION

Plants of the new *Mandevilla* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Lancalifornia'. These characteristics in combination distinguish 'Lancalifornia' as a new and distinct *Mandevilla* plant:

1. Compact plant habit.
2. Moderately vigorous to vigorous growth habit.
3. Glossy dark green-colored leaves.
4. Early and freely flowering habit.
5. Large yellow-colored flowers.

Plants of the new *Mandevilla* can be compared to plants of the female parent, 'Rosea Foncé'. Plants of the new *Mandevilla* differ primarily from plants of 'Rosea Foncé' in flower color as plants of 'Rosea Foncé' have pink-colored flowers.

Plants of the new *Mandevilla* can be compared to plants of the male parent selection. Plants of the new *Mandevilla* differ primarily from plants of the male parent selection in flower color as plants of the male parent selection have rose pink-colored flowers.

Plants of the new *Mandevilla* can be compared to plants of selections of *Mandevilla Sanderi* known to the Inventor, not patented. In side-by-side comparisons conducted in Malause, France, plants of the new *Mandevilla* differed from plants of selections of *Mandevilla Sanderi* known to the Inventor primarily in flower color as plants of selections of *Mandevilla Sanderi* known to the Inventor had rose pink or white-colored flowers.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet comprises a side perspective view of a typical flowering plant of 'Lancalifornia' grown in a container.

The photograph on the second sheet is a close-up view of typical flower of 'Lancalifornia'.

DETAILED BOTANICAL DESCRIPTION

The aforementioned photographs and following observations, measurements and values describe plants grown during the autumn in two-liter containers in polyethylene-covered greenhouse in Malause, France and under cultural practices typical of *Mandevilla* commercial production. During the production of the plants, day temperatures ranged from 8° C. to 26° C. and night temperatures ranged from 3° C. to 15° C.

Plants were six months old when the photographs and description were taken. In the following description, color references are made to The Royal Horticultural Society Colour Chart, 2007 Edition, except where general terms of ordinary dictionary significance are used.

Botanical classification: *Mandevilla Sanderi* 'Lancalifornia'.

Parentage:

*Female, or seed, parent.*—*Mandevilla Sanderi* 'Rosea Foncé', not patented.

*Male, or pollen, parent.*—Unnamed selection of *Mandevilla Sanderi*, not patented.

Propagation:

*Type.*—By vegetative cuttings.

*Time to initiate roots, summer.*—About two weeks at 23° C. to 25° C.

*Time to initiate roots, winter.*—About three weeks at 23° C. to 25° C.

*Time to produce a rooted young plant, summer.*—About five to six weeks at 23° C. to 25° C.

*Time to produce a rooted young plant, winter.*—About six to eight weeks at 23° C. to 25° C.

*Root description.*—Fibrous, fine; light yellowish white in color.

*Rooting habit.*—Freely branching; medium density.

Plant description:

*Plant and growth habit.*—Compact plant habit; upright to outwardly spreading; moderately vigorous to vigorous growth habit.

*Plant height.*—About 19.6 cm.

*Plant diameter (spread).*—About 51.5 cm.

*Lateral branch description.*—Branching habit: Moderately freely branching habit with about five lateral branches developing per plant; pinching enhances lateral branch development. Length: About 32.7 cm. Diameter: About 2 mm. Internode length: About 3.1 cm. Strength: Strong. Texture: Smooth, glabrous. Color: Close to 144A tinged with close to 174C on upper side; older stems, close to 200C.

Foliage description:

*Arrangement.*—Opposite, simple.

*Length.*—About 5.9 cm.

*Width.*—About 3.8 cm.

*Shape.*—Obovate.

*Apex.*—Abruptly acute.

*Base.*—Truncate.

*Margin.*—Entire.

*Texture, upper and lower surfaces.*—Smooth, glabrous; glossy.

*Venation pattern.*—Pinnate, reticulate.

*Color.*—Developing leaves, upper and lower surfaces: Close to 152A. Full expanded leaves, upper surface: Close to N137B; venation, close to 146B. Fully expanded leaves, lower surface: Between 137B and 146A; venation, close to 146D.

*Petiole length.*—About 6 mm.

*Petiole diameter.*—About 2 mm.

*Petiole texture, upper surface.*—Smooth, glabrous.

*Petiole texture, lower surface.*—Densely pubescent.

*Petiole color, upper and lower surfaces.*—Close to 138B.

Flower description:

*Flower type and flowering habit.*—Single salverform flowers arranged in axillary racemes; flowers star-shaped and face mostly outwardly; freely flowering habit with about twelve flowers developing per inflorescence and about 120 flowers developing per plant.

*Natural flowering season.*—Early flowering habit with plants begin to flower about six weeks after planting; plants flower continuously from summer into the autumn in France.

*Flower longevity on the plant.*—About seven days; flowers not persistent.

*Fragrance.*—Faint, somewhat unpleasant.

*Flowers.*—Appearance: Flared trumpet, corolla fused and five-parted. Diameter: About 10 cm. Depth (length): About 6.8 cm. Tube length: About 6.2 cm.

*Flower buds.*—Length: About 3.5 cm. Diameter: About 7 mm. Shape: Narrowly obovate. Color: Mid-section, close to 145A; towards the apex and base, close to 143C.

*Corolla.*—Quantity and arrangement: Five petals arranged in a single whorl and fused at the base. Petal length: About 10.4 cm. Petal width: About 3.9 cm. Petal shape and appearance: Roughly spatulate; lower 60% of the petal is fused. Petal apex: Rounded. Petal margin: Entire. Petal texture, upper and lower surfaces: Smooth, glabrous; slightly velvety. Throat texture: Smooth, glabrous. Tube texture: Smooth, glabrous. Color: Petal, when opening, upper surface: Between 12A an 13A; throat, close to 17C, towards the base of the throat, close to 144C. Petal, when opening, lower surface: Between 13B and 14B; tube, close to 154C, towards the base of the tube, close to 144C. Petal, fully opened, upper surface: Close to 13B; throat, close to 17A to 17B, towards the base of the throat, close to 144C. Petal, fully opened, lower surface: Close to 13B to 13C; tube, close to 11B, towards the base of the tube, close to 144C.

*Corona.*—Quantity and arrangement: Five sepals arranged in a single whorl. Sepal length: About 1 mm. Sepal width: About 1 mm. Sepal shape: Deltoid. Sepal apex: Broadly acuminate. Sepal base: Roughly truncate. Sepal margin: Entire. Sepal texture, upper and lower surfaces: Smooth, glabrous.

*Sepal color.*—Immature and mature, upper surface: Close to 144C. Immature and mature, lower surface: Close to 144C.

*Peduncles.*—Length: About 1.2 cm. Diameter: About 2.5 mm. Texture: Smooth, glabrous. Strength: Flexible, but strong. Color: Close to 144C.

*Pedicels.*—Length: About 2 cm. Diameter: About 2 mm. Texture: Smooth, glabrous. Strength: Flexible, but strong. Color: Close to 144C.

*Reproductive organs.*—Stamens: Quantity and arrangement: Typically five; basifixed; anthers connivent. Filament length: About 1 mm. Anther shape: Ellipsoidal. Anther length: About 7 mm. Anther color: Close to 158A. Pollen amount: None observed. Pistils: Quantity: Typically one. Pistil length: About 3 cm. Style length: About 2.95 cm. Style color: Close to 155A, towards the base, close to 157D. Stigma shape: Flattened. Stigma color: Close to 155A. Ovary color: Close to 144C.

*Seeds and fruits.*—Seed and fruit production have not been observed on plants of the new *Mandevilla*.

Disease & pest resistance: Plants of the new *Mandevilla* have not been noted to be resistant to pathogens and pests common to *Mandevilla* plants.

Temperature tolerance: Plants of the new *Mandevilla* have been observed to tolerate high temperatures of about 40° C. and to be hardy to USDA Hardiness Zone 9.

It is claimed:

1. A new and distinct *Mandevilla* plant named 'Lancalifornia' as illustrated and described.

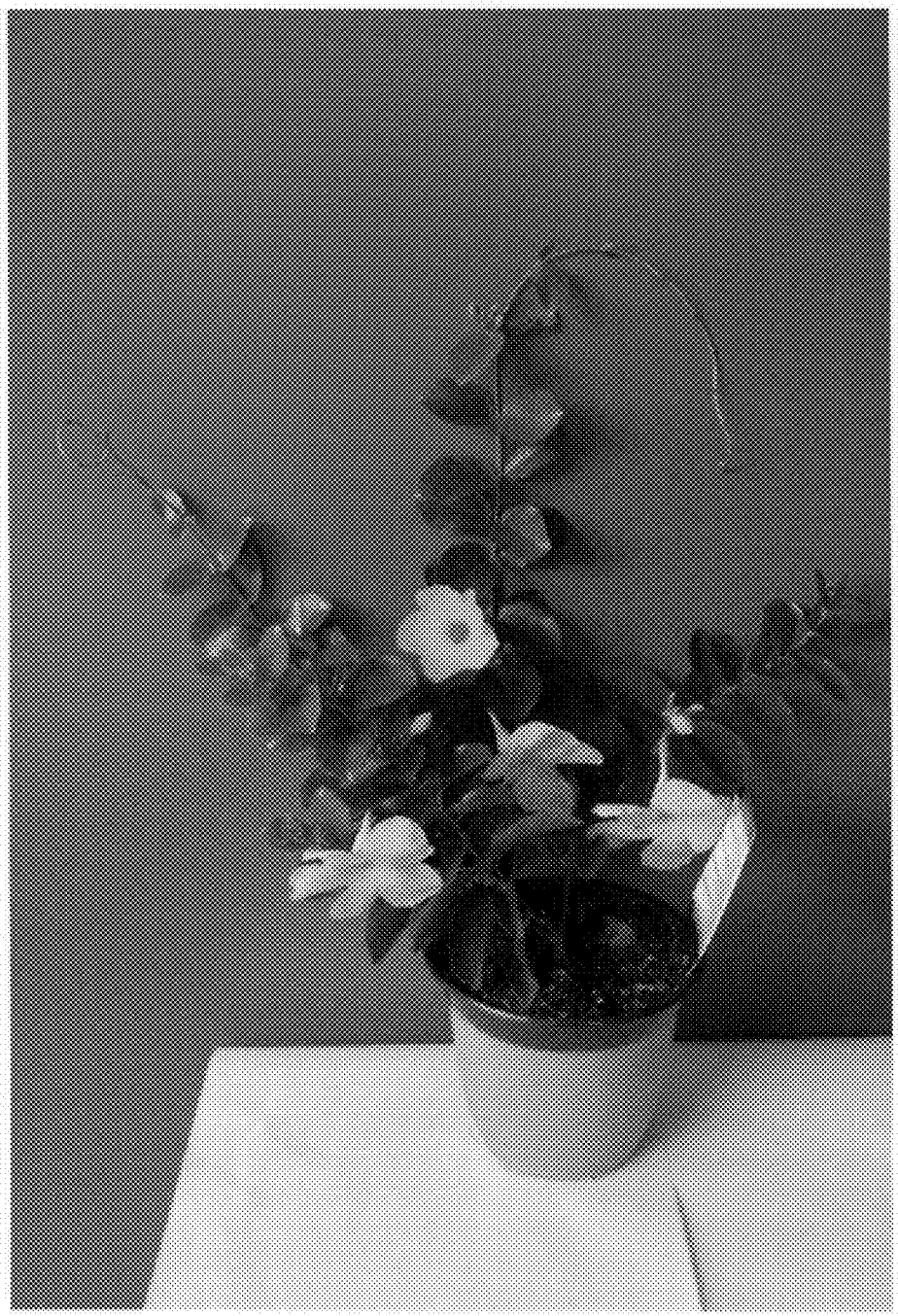

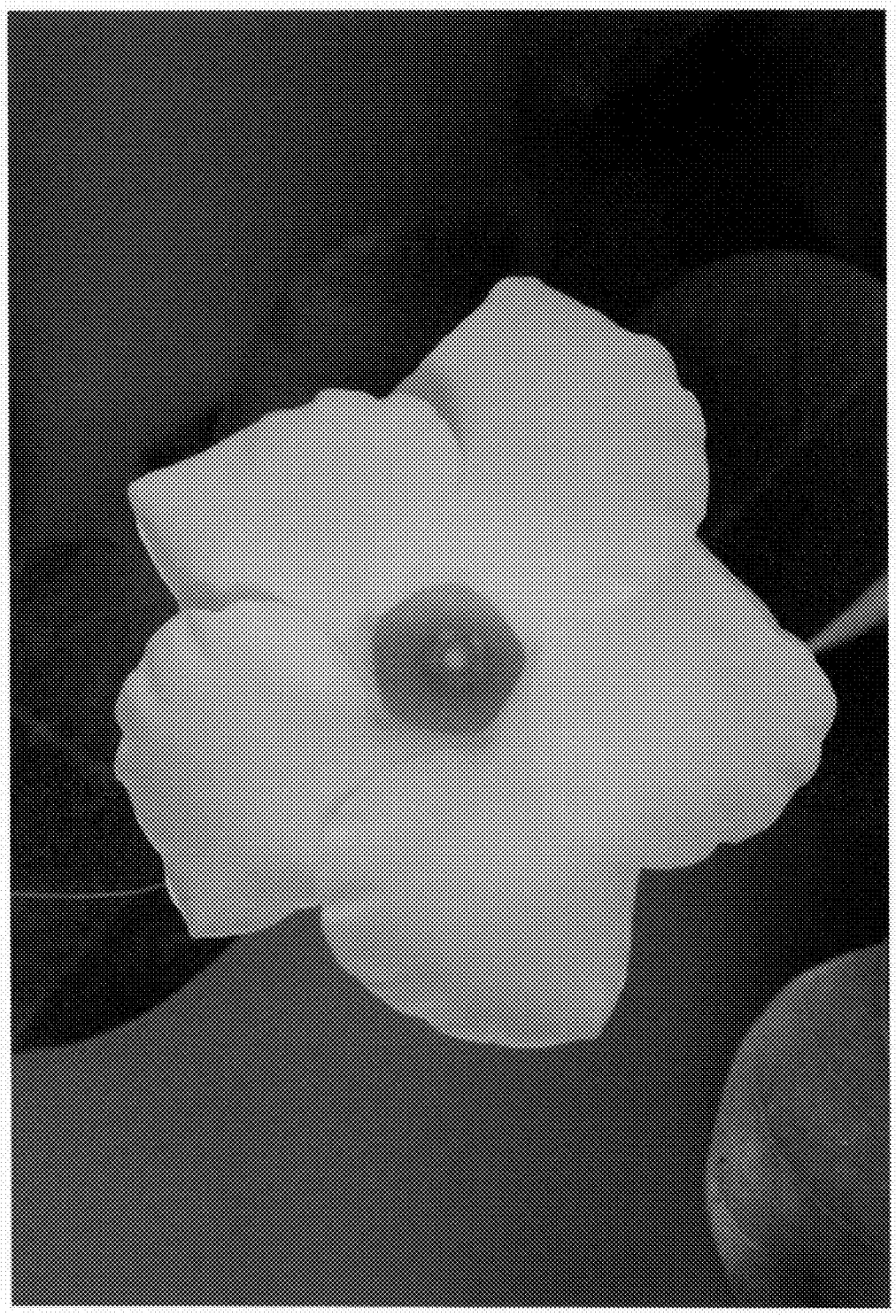

* * * * *